United States Patent [19]

Megchelsen et al.

[11] Patent Number: 5,786,058
[45] Date of Patent: Jul. 28, 1998

[54] THERMALLY BONDED VIRAL BARRIER COMPOSITE

[76] Inventors: Sara L. Megchelsen; Nancy C. Rauschenberg; Mark V. Johnson, all of P.O. Box 33427, St. Paul, Minn. 55133-3427

[21] Appl. No.: 571,468

[22] Filed: Dec. 13, 1995

Related U.S. Application Data

[62] Division of Ser. No. 415,530, Apr. 3, 1995, abandoned.

[51] Int. Cl.$^6$ ........................................ B32B 5/18
[52] U.S. Cl. ........................ 428/57; 442/397; 442/398; 442/401; 2/456
[58] Field of Search .................... 428/57, 286, 297, 428/302, 304.4, 315.5, 315.9, 318.4; 442/394, 397, 398, 401; 2/456

[56] References Cited

U.S. PATENT DOCUMENTS

| | | | |
|---|---|---|---|
| 3,426,754 | 2/1969 | Bierenbaum et al. | 128/156 |
| 3,801,404 | 4/1974 | Druin et al. | 156/229 |
| 3,801,692 | 4/1974 | Zimmerman | 264/210 R |
| 3,839,240 | 10/1974 | Zimmerman | 260/2.5 HA |
| 3,843,761 | 10/1974 | Bierenbaum et al. | 264/210 R |
| 3,844,865 | 10/1974 | Elton et al. | 156/229 |
| 3,870,593 | 3/1975 | Elton et al. | 161/159 |
| 3,953,566 | 4/1976 | Gore | 264/288 |
| 3,962,153 | 6/1976 | Gore | 260/2.5 R |
| 4,041,203 | 8/1977 | Brock et al. | 428/157 |
| 4,096,227 | 6/1978 | Gore | 264/210 R |
| 4,194,041 | 3/1980 | Gore et al. | 428/315 |
| 4,196,245 | 4/1980 | Kitson et al. | 428/198 |
| 4,270,658 | 6/1981 | Schuster | 206/439 |
| 4,347,844 | 9/1982 | Ohki et al. | 128/287 |
| 4,374,888 | 2/1983 | Bornslaeger | 428/198 |
| 4,374,889 | 2/1983 | Arens | 428/207 |
| 4,379,192 | 4/1983 | Wahlquist et al. | 428/156 |
| 4,419,993 | 12/1983 | Petersen | 128/201.15 |

(List continued on next page.)

FOREIGN PATENT DOCUMENTS

| | | | |
|---|---|---|---|
| 260 011 A2 | 3/1988 | European Pat. Off. | |
| 0 505 027 A1 | 9/1992 | European Pat. Off. | D04H 13/00 |
| S.60-142860 | 7/1985 | Japan. | |
| 63-276533 A1 | 11/1988 | Japan | B32B 5/32 |
| S.64-22305 | 1/1989 | Japan. | |
| H.1-305001 | 12/1989 | Japan. | |
| H.2-212527 | 8/1990 | Japan. | |
| 2149343 | 6/1985 | United Kingdom. | |
| 2232905 | 1/1995 | United Kingdom. | |

(List continued on next page.)

OTHER PUBLICATIONS

D.J. Bucheck, "Comfortable clothes through chemistry", *Chemtech*, 21, 142–147 (1991).
E.A. McCullough et al., "Liquid Barrier Properties of Nin Surgical Gown Fabrics", *INDA JNR*, 3, 14–20 (1991).
A.L. Panlilio et al., "Blood Contacts During Surgical Procedures", *JAMA*, 265, 1533–1537.
ASTM Designation: E 96–80, "Standard Test Methods for Water Vapor Transmission of Materials", pp. 738–745 (Feb. 1981).

(List continued on next page.)

*Primary Examiner*—Marion E. McCamish
*Assistant Examiner*—Elizabeth M. Cole
*Attorney, Agent, or Firm*—Gary L. Griswold; Walter N. Kirn; William J. Bond

[57] ABSTRACT

A viral barrier composite of a thermoplastic film thermally bonded on at least one side thereof to a breathable thermoplastic web, and method for making the same. The viral barrier composite has viral barrier properties, a moisture vapor transmission rate of at least 700 g/m$^2$/24 hours and a bond strength between the thermoplastic film and breathable thermoplastic web of at least 0.07N/cm. The viral barrier composite is formed by calendering an assembly comprising a thermoplastic film and a breathable thermoplastic web between a smooth roll and a pattern roll. The viral barrier composite may be used for constructing articles of protective apparel.

16 Claims, 6 Drawing Sheets

U.S. PATENT DOCUMENTS

| | | | |
|---|---|---|---|
| 4,433,026 | 2/1984 | Molde | 428/252 |
| 4,443,511 | 4/1984 | Worden et al. | 428/198 |
| 4,515,841 | 5/1985 | Dyke | 428/35 |
| 4,519,909 | 5/1985 | Castro | 210/500.2 |
| 4,539,256 | 9/1985 | Shipman | 428/315.5 |
| 4,542,771 | 9/1985 | Payet et al. | 139/302 |
| 4,555,293 | 11/1985 | French | 156/308.4 |
| 4,609,584 | 9/1986 | Cutler et al. | 428/156 |
| 4,613,544 | 9/1986 | Burleigh | 428/315.5 |
| 4,644,586 | 2/1987 | Padgett | 383/102 |
| 4,705,812 | 11/1987 | Ito et al. | 521/92 |
| 4,726,989 | 2/1988 | Mrozinski | 428/315.5 |
| 4,777,073 | 10/1988 | Sheth | 428/155 |
| 4,824,718 | 4/1989 | Hwang | 428/284 |
| 4,828,556 | 5/1989 | Braun et al. | 604/365 |
| 4,845,779 | 7/1989 | Wheeler et al. | 2/84 |
| 4,847,142 | 7/1989 | Twilley et al. | 428/252 |
| 4,863,792 | 9/1989 | Mrozinski | 428/315.5 |
| 4,867,881 | 9/1989 | Kinzer | 210/490 |
| 4,877,679 | 10/1989 | Leatherman et al. | 428/224 |
| 4,898,761 | 2/1990 | Dunaway et al. | 428/137 |
| 4,913,772 | 4/1990 | Taylor et al. | |
| 4,920,960 | 5/1990 | Hubbard et al. | 182/206.12 |
| 4,929,303 | 5/1990 | Sheth | 156/209 |
| 4,937,115 | 6/1990 | Leatherman | 428/36.4 |
| 4,954,256 | 9/1990 | Degen et al. | 210/490 |
| 4,961,985 | 10/1990 | Henn et al. | 428/196 |
| 4,975,469 | 12/1990 | Jacoby et al. | 521/84.1 |
| 4,976,274 | 12/1990 | Hanssen | 128/849 |
| 4,983,450 | 1/1991 | Yanagihara et al. | 428/283 |
| 5,013,439 | 5/1991 | Fisher et al. | 210/500.23 |
| 5,017,292 | 5/1991 | DiLeo et al. | 210/645 |
| 5,025,052 | 6/1991 | Crater et al. | 524/104 |
| 5,026,591 | 6/1991 | Henn et al. | 428/198 |
| 5,032,450 | 7/1991 | Rechlicz et al. | 428/196 |
| 5,043,209 | 8/1991 | Boissé et al. | 428/233 |
| 5,045,133 | 9/1991 | DaPonte et al. | 156/62.8 |
| 5,055,338 | 10/1991 | Sheth et al. | 428/155 |
| 5,110,506 | 5/1992 | Ciallella | 252/559 |
| 5,114,787 | 5/1992 | Chaplin et al. | 428/284 |
| 5,116,650 | 5/1992 | Bowser | 428/34.2 |
| 5,120,594 | 6/1992 | Mrozinski | 428/195 |
| 5,126,189 | 6/1992 | Tanny et al. | 428/220 |
| 5,134,017 | 7/1992 | Baldwin et al. | 428/198 |
| 5,156,780 | 10/1992 | Kenigsberg et al. | 264/22 |
| 5,169,712 | 12/1992 | Tapp | 428/315.5 |
| 5,176,953 | 1/1993 | Jacoby et al. | 428/315.5 |
| 5,178,932 | 1/1993 | Perkins et al. | 428/198 |
| 5,187,005 | 2/1993 | Stahle et al. | 428/252 |
| 5,208,098 | 5/1993 | Stover | 428/284 |
| 5,260,360 | 11/1993 | Mrozinski et al. | 524/95 |
| 5,264,276 | 11/1993 | McGregor et al. | 428/252 |
| 5,308,691 | 5/1994 | Lim et al. | 428/286 |
| 5,317,035 | 5/1994 | Jacoby et al. | 521/143 |
| 5,352,108 | 10/1994 | Kagawa et al. | 425/174.4 |
| 5,352,513 | 10/1994 | Mrozinski et al. | 428/315.5 |
| 5,393,603 | 2/1995 | Toyoda et al. | 428/316.6 |
| 5,409,761 | 4/1995 | Langley | 428/198 |
| 5,532,053 | 7/1996 | Mueller | |
| 5,560,974 | 10/1996 | Langley | 428/198 |
| 5,589,249 | 12/1996 | Bodford et al. | 428/220 |

FOREIGN PATENT DOCUMENTS

| | | | |
|---|---|---|---|
| WO 93/07914 | 4/1993 | WIPO | A16L 31/00 |
| WO 93/08019 | 4/1993 | WIPO | B32B 3/00 |
| WO 95/03172 | 2/1995 | WIPO | B32B 7/04 |
| WO 95/16562 | 6/1995 | WIPO | B32B 5/24 |
| WO 95/23696 | 9/1995 | WIPO | B32B 27/08 |
| WO 96/09165 | 3/1996 | WIPO | |
| WO 96/16562 | 6/1996 | WIPO | |
| WO 96/31345 | 10/1996 | WIPO | B32B 27/32 |

OTHER PUBLICATIONS

ASTM Designation: D 726–84, "Standard Test Methods for Resistance of Nonporous Paper to Passage of Air", pp. 64–65 (May 1984).

ASTM Designation: D 5035–90, "Standard Test Method for Breaking Force and Elongation of Textile Fabrics (Strip Force)", pp. 732–737 (May 1990).

ASTM Designation: ES 22–92, "Emergency Standard Test Method for Resistance of Protective Clothing Materials to Penetration by Blood–Borne Pathogens Using Viral Penetration as a Test System", pp. 1–7 (Nov. 1992).

ASTM Designation: ES 21–92, "Emergency Standard Test Method for Resistance of Protective Clothing Materials to Synthetic Blood", pp. 1–4 (Nov. 1992).

5,786,058

1
THERMALLY BONDED VIRAL BARRIER COMPOSITE

This is a division of application Ser. No. 08/415,530 filed Apr. 4, 1995, now abandoned.

FIELD OF THE INVENTION

The present invention is directed to a thermally bonded viral barrier composite, and a method of manufacturing the same.

DESCRIPTION OF THE RELATED ART

Surgical gowns, drapes, masks, gloves, sterile wraps, wound dressings, waste disposal bags, and other medical products require viral barrier properties combined with breathability. Liquid repellency is recognized as an important property in assuring that these products act as a barrier against the passage of bacteria or viruses carried in liquids. For example, body liquids and other fluids can permeate through a surgical gown or drape lacking liquid repellency properties. In addition to being liquid repellent and a bacteria and viral barrier, it has been widely recognized that these products must be breathable to be comfortable to the wearer. Water vapor from perspiration should be transmitted from inside to outside of the material so that the natural evaporative cooling effect can be achieved. For example, in a continuous film of hydrophilic material, water vapor is effectively transported through the film on a molecule by molecule basis.

One type of material commonly used for protective clothing is made from a nonwoven substrate calendered at high temperature and pressure. While having reasonable properties for protection, these garments are known to be very uncomfortable due to their inherently low moisture vapor transmission and low air permeability characteristics.

A microporous membrane with viral barrier capabilities and breathability is described in U.S. Pat. No. 5,260,360 to Mrozinski et al. Mrozinski discloses a polymeric microporous membrane having a matrix of pores forming continuous passages through the thickness of the membrane and opening on the opposite surface thereof. The addition of fluorochemical to the microporous membrane reduces the surface energy of the membrane, thereby increasing the numerical difference between the surface energy of the membrane and liquid contaminants.

The comfort and durability of microporous membranes, such as the membrane disclosed in Mrozinski, or other breathable viral barrier films can be significantly enhanced by laminating the membrane to suitable reinforcing webs, such as spunbond webs. However, the laminating process may compromise the viral barrier capabilities or breathability of the microporous membrane. For example, use of an adhesive to laminate a reinforcing web to a microporous membrane can be problematic where the adhesive contains solvents reactive with the microporous membrane. Additionally, the solvents in some adhesives present environmental hazards, which increase the cost of the product.

Thermal or ultrasonic bonding of a microporous membranes may create pinholes in the membrane and diminish the viral barrier capabilities. Thermal or ultrasonic bonding may also collapse the micropores and unacceptably reducing the breathability and moisture vapor transmission properties of the webs.

One possible reinforcing web is a bonded spunbond web, which is manufactured by calendering unbonded spunbond fibers to form a tighter matrix of fibers that is smooth, soft and abrasion resistant. Previous attempts to thermally bond a 34 grams/m$^2$ (1 ounce/yd$^2$) bonded spunbond web to a microporous membrane using a heated point-bonding roll (approximately 15% point contact) and a heated smooth roll calendering roll (nip gap 0.002 to 0.0508 mm) resulted in an unacceptably low bond strength in the range of 0.012 to 0.018N/cm.

Alternatively, unbonded spunbond may be used for the reinforcing web. Unbonded spunbond is essentially extruded thermoplastic fibers deposited onto a moving belt that are allowed to harden without performing a calendering operation. Unbonded spunbond, while exhibiting good bonding characteristics, has low tensile strength. Additionally, unbonded spunbond webs have a coarse finish which is both uncomfortable to wear and provide minimal resistance to abrasion.

A related problem exists with regard to creating seams for assembling protective apparel that are both strong and resistant to the transmission of viral pathogens. For example, the strength of sleeve seams and sleeve attachment seams on surgical gowns is critical due to the significant stresses encountered by sleeves during use.

Protective apparel containing sewn seams can have needle holes which greatly reduce the effectiveness of the viral barrier in the seam area. Thus, bacteria and viruses, such as the immunodeficiency virus or Hepatitis B virus, which may be present on the surface of the protective apparel, can be transmitted through the needle holes. One approach to creating viral resistant seams includes interposing an elastomeric material between the overlapping fabric at the seam. The highly resilient nature of the elastomeric material causes it to return to its original position after the sewing needle is removed, so as to provide a better barrier to viral pathogens.

Ultrasonic welding has also been used to produce less permeable seams for protective apparel. However, some ultrasonic welding techniques create seam structures that lack the tensile strength necessary for certain protective apparel, requiring a secondary reinforcing operation, such as the application of a viral barrier adhesive tape over the seam.

The V-shaped ultrasonic welding wheel 10 and ultrasonic generator 15 of FIG. 1 provides a thin, comfortable weld for use in protective apparel. The sloped welding area 11 cuts and seals the seam at the edge of the wheel 10. However, the small surface area and sloped configuration of the welding area 11 produces a relatively small quantity of molten thermoplastic material so that welding speed is generally reduced for seams of acceptable tensile strength.

Alternatively, the ultrasonic welding wheel 12 shown in FIG. 2 relies on a relatively large solid seal area 13 and intermittent feed notches 14 to produce a greater quantity of molten thermoplastic material. The large solid seal area 13 allows the welding wheel 12 to achieve higher speeds. However, the feed notches 14 of the weld wheel 12 of FIG. 2 creates an intermittent row of seal lines or a stitch patterns adjacent to the solid seal weld line. The resulting seam has a width "w" which is generally stiff and uncomfortable to wear.

SUMMARY OF THE INVENTION

The present invention is directed to a viral barrier composite, and method for manufacturing the same. The composite may be used for a variety of protective apparel, such as surgical gowns, drapes, masks, gloves, sterile wraps, wound dressings, waste disposal bags or other products requiring viral barrier properties.

The viral barrier composite is formed by thermally bonding a thermoplastic film on at least one side thereof to a breathable polymeric web. The resulting composite has viral barrier properties and a moisture vapor transmission rate of at least 700 g/m$^2$/24 hours. The bond strength between the polymeric film and thermoplastic web is at least 0.07 N/cm (0.04 lbs/inch). The composite has an air permeability expressed as Gurley porosity of less than 1000 seconds/50 cc, and preferably less than 500 seconds/50 cc. The breathable thermoplastic web may be woven or nonwoven fibrous materials made of poyolefins, polyethylene, polypropylene, polybutylene and combinations thereof.

In one embodiment, the polymeric film is a thermoplastic polymer and a water- and oil-repellent fluorochemical compound that forms a microporous membrane with oleophobic and hydrophobic properties. Less than 100 viruses, preferably less than 10 viruses, and most preferably no viruses are permitted to pass through the viral barrier composite according to ASTM Test Method ES 22-1992. The microporous membrane is polypropylene and the thermoplastic web is a bonded spunbond nonwoven polypropylene web.

The present invention is also directed to an article of protective apparel constructed from the viral barrier composite. The article of protective apparel may have at least one reinforced viral resistant seam. The viral resistant seam includes a first viral barrier composite having a first attachment edge and a second viral barrier composite having a second attachment edge arranged with the first composite viral barrier to form a common seam edge extending along the first and second attachment edges. At least one reinforcing strip constructed from a thermoplastic material extending along the common seam edge is thermally bondable with the first and second viral barrier composite. An ultrasonic weld bonds the first and second attachment edges and the reinforcing strip extending along a seal edge to form the reinforced viral resistant seam.

The present invention is also directed to a process for thermally bonding a viral barrier composite by calendering an assembly of a thermoplastic film and a breathable thermoplastic web between a smooth roll and a pattern roll so that the bond strength between the thermoplastic film and thermoplastic web is at least 0.07N/cm and the resulting composite has viral barrier properties and a moisture vapor transmission rate of at least 700 g/m$^2$/24 hours. In the preferred embodiment, the thermoplastic film is positioned to contact the smooth roll and the breathable thermoplastic web is positioned to contact a pattern roll.

The surface speed of the smooth roll and pattern roll at a nip point may be between 3–200 meters/minute, and preferably between 20–100 meters/minute. The temperature of each calendering roll is in the range of approximately 100°–200° C. The pressure at a nip point between the smooth roll and the pattern roll is approximately 5–50 N/mm. The pattern roll has a percent bonding surface area of approximately 7–30%, and preferably between 15–25%. In an embodiment where the pattern roll is a point bonding roll, the density of the bonding points on the point bonding roll is approximately 1.75 to 150 points/cm$^2$. The surface area of the bonding points on the point bonding roll is about 4.0–0.20 mm$^2$. The air permeability expressed as Gurley porosity is less than 1000 seconds/50 cc, preferably less than 500 seconds/50 cc, and most preferably less than 200 seconds/50 cc.

The process also includes forming a viral resistant seam between two sheets of the viral barrier composite. First and a second attachment edges of a first and a second viral barrier composites, respectively, are arranged to form a common seam edge. A reinforcing strip is positioned to extend along the common seam edge. The reinforcing strip is constructed of a thermoplastic material thermally bondable with the first and second viral barrier composites. An ultrasonic weld is formed along a seal edge to connect the first and second attachment edges and the reinforcing strip, so that the viral resistant seam is formed. The ultrasonic welding wheel has a cutting edge immediately adjacent to a welding surface and an ultrasonic generator. The continuous surface of the weld wheel extrudes molten thermoplastic material into the fibers of the spunbond laminate adjacent to the viral resistant seam.

The present invention relates to a reinforced ultrasonic seam for protective apparel that resists the transmission of viral pathogens, and a method of manufacturing the same. The viral resistant seam has a low surface area and a high tensile strength that increases comfort and functionality.

In a first embodiment, the reinforced viral resistant seam for protective apparel includes a first and second webs arranged to form a common seam edge extending along first and second attachment edges. At least one reinforcing strip constructed of a material thermally bondable to the webs is arranged along the common seam edge. An ultrasonic weld is formed along the common seam edge. The ultrasonic weld line is located immediately adjacent to the seal edge to create a low surface area reinforced viral resistant seam.

The reinforced viral resistant seam may be useful with a variety of materials, such as poyolefins, polypropylene, polyethylene, polybutylene, copolymers and combinations thereof, and the present viral barrier composites. The first and second webs may be a variety of thermoplastic polymers, such as a bilaminate or trilaminate composites constructed from a polypropylene microporous film laminated to polypropylene spunbond nonwoven fiber. The reinforcing strip may also be a thermoplastic material, such as polypropylene.

The present low surface area reinforced viral resistant seam may be used to assemble any seam of the protective apparel, although it is particularly useful for attaching sleeves to the body portion of a surgical gown.

The method for forming a low surface area reinforced viral resistant seam includes arranging a first and second webs to form a common seam edge extending along the first and second attachment edges thereof. At least one reinforcing strip is positioned along the common seam edge. The reinforcing strip(s) preferably includes a thermoplastic material thermally bondable with the thermoplastic material contained in the first and second webs. An ultrasonic weld is formed along a seal edge.

The step of forming an ultrasonic weld includes passing the common seam edge of the reinforcing strip and webs between an ultrasonic welding wheel and an ultrasonic generator. One embodiment of the ultrasonic welding wheel includes a weld surface generally parallel to the plane of the reinforcing strip and webs and immediately adjacent to a cutting edge.

The welding wheel permits feeding the present viral barrier composite at rates of approximately 12.0 meters/min. The weld area extrudes molten thermoplastic material into the fibers of the spunbond laminate. The critical dimension between the welding surface and ultrasonic generator affects the degree to which the fibers laminated to the viral barrier composite near the weld area are weakened and the quantity of molten thermoplastic material produced by the ultrasonic process. If the critical dimension is too small, the fibers near the weld degrade, weakening the seam. Alternatively, if the critical dimension is too large, an insufficient quantity of molten thermoplastic material will be produced by the welding process, resulting in a weak seam.

Definitions as used in this application:

"Bilaminate" means a microporous membrane or other breathable film laminated on one side thereof to a woven or nonwoven web. For example, spunbond polypropylene nonwoven web laminated to a polypropylene microporous membrane.

"Critical dimension" means the distance between the solid seal area of the welding wheel and the ultrasonic generator.

"Hydrophobic" describes materials which are not wet by liquid water or aqueous body fluids and which are capable of repelling and preventing the passage of liquid water through their structure.

"Heat sealable" is used herein to describe materials having a thermoplastic component that can be sealed together using a hot bar, ultrasonic, or other thermal process sealer.

"Moisture vapor permeable" is used herein to describe materials which readily permit the passage of water vapor through the membrane but do not allow the passage of liquid water.

"Oleophobic" describes materials which are not wet by oil, grease, or body fluids, which contain oily components, and are capable of preventing the passage of oils and grease through their structure.

"Bond strength" means the force required to delaminate a multilayered material.

"Protective apparel" means surgical gowns, drapes, masks, gloves, sterile wraps, wound dressings, shoe covers, neck gaiters, sleeve covers, waste disposal bags, or other products requiring some viral resistant or barrier properties.

"Thermoplastic" means a polymeric material having a thermoplastic component which may include polyolefins, polyesters, polyetheresters, and polyamides. Examples of suitable thermoplastic polymers include, by way of illustration only, such polyolefins as polyethylene, polypropylene, poly(1-butene), poly(2-butene), poly(1-pentene), poly(2-pentene), poly(3-methyl-1-pentene), poly(4-methyl-1-pentene), 1,2-poly-1,3-butadiene, 1,4-poly-1,3-butadiene, polyisoprene, polychloroprene, polyacrylonitrile, poly(vinyl acetate), poly(vinylidene chloride), polystyrene, and the like; such polyesters as poly(ethylene terephthalate), poly(tetramethylene terephthalate), poly(cyclohexylene-1,4-dimethylene terephthalate) or poly(oxymethylene-1,4-cyclohexylenemethyleneoxyterephthaloyl), and the like; such polyetheresters as poly(oxyethylene)-poly(butylene terephthalate), poly(oxytrimethylene)-poly(butylene terephthalate), poly(oxytetramethylene)-poly(butyleneterephthalate), poly(oxytetramethylene)-poly(ethylene terephthalate), and the like; and such polyamides as poly(6-aminocaproic acid) or poly(,-caprolactam), poly(hexamethylene adipamide), poly(hexamethylene sebacamide), poly(11-aminoundecanoic acid), and the like.

"Trilaminate" means a microporous membrane or other breathable film laminated on both side thereof to a woven or nonwoven web. For example, spunbond polypropylene nonwoven webs laminated to a polypropylene microporous membrane.

"Water repellent" describes materials which are not water wettable and are capable of preventing the passage of liquid water through the material by capillary action under varying ambient atmospheric conditions, including water impinging on the surface of the membrane.

DETAILED DESCRIPTION OF THE PREFERRED EMBODIMENTS

Figure 1:
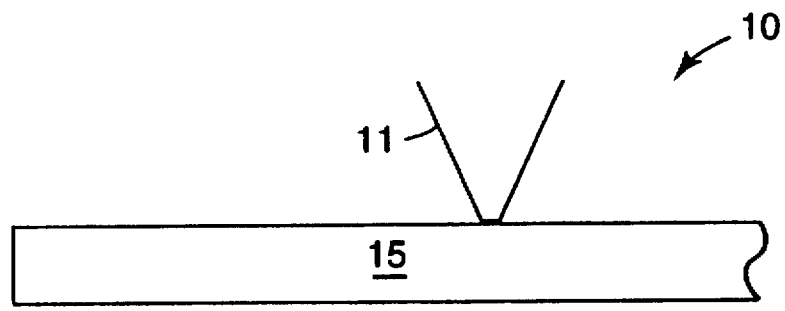
FIG. 1 is a schematic illustration of a prior art V-shaped weld wheel design.
Figure 2:
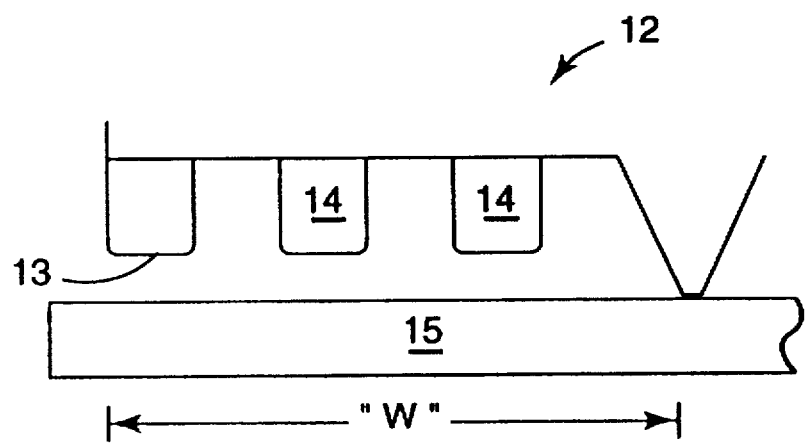
FIG. 2 is a schematic illustration of an alternate prior art weld wheel design.

The present invention is directed to a thermally bonded viral barrier composite, and a method for manufacturing the same. The viral barrier component of the present viral barrier composite may include various films or microporous membranes with viral barrier properties, such as a monolithic film sold under the tradename Hytrel from E. I. duPont de Nemours and Company of Wilmington, Del. or a microporous membrane described in U.S. Pat. No. 5,260,360 to Mrozinski et al., which is hereby incorporated by reference.

Microporous membranes useful in the present invention may have a microporous structure generally characterized by a multiplicity of space, separated, randomly dispersed, nonuniform shaped, equiaxed particles of polyolefin connected by fibrils which are intimately surrounded by the processing compound and the fluorochemical. The microporous membrane is preferably liquid repellent, moisture vapor and air permeable and has viral barrier capabilities. The viral barrier characteristics of the microporous membrane described in U.S. Pat. No. 5,260,360 to Mrozinski et al., are disclosed in PCT application No. WO 93/07914 published on Apr. 29, 1993 and U.S. patent application Ser. No. 08/384,079 entitled A METHOD FOR PREVENTING TRANSMISSION OF VIRAL PATHOGENS, filed Feb. 6, 1995, which is hereby incorporated by reference.

The strength and durability of many microporous membranes and other viral barrier films may be increased by laminating the membrane or film to a suitable substrate or web. Additionally, if the membrane or film is used for protective apparel, the substrate or web can enhance comfort for the wearer. For example, a suitable substrate may be a web of woven or nonwoven thermoplastic fibers.

Suitable fibrous non-woven webs include ethylene-propylene copolymer, high density polyethylene, low density polyethylene, linear low density polyethylene, polyamides, polyesters, a blend of polypropylene and polybutene, and a blend of polypropylene and linear low density polyethylene, although it will be understood that various woven and nonwoven webs may serve this purpose. In the embodiment discussed below, the reinforcing substrate is at least one layer of a bonded spunbond nonwoven polypropylene web. The fibers of the bonded spunbond web have an average diameter of approximately 20 micrometers and the spunbond web has an average weight of 34 grams/m$^2$ (1 ounce/yard$^2$), although spunbond in the range of 14–68 grams/m$^2$ (0.4–2.0 ounce/yard$^2$) may be used. A bonded spunbond nonwoven polypropylene web suitable for lamination to the polypropylene microporous membrane may be obtained from Poly-Bond, Inc., of Waynesboro, Va.

The present thermal bonding process represents a balance of various factors, including maintaining an adequate bond strength between the web(s) and the microporous membrane or viral barrier film, minimizing pinholes that decrease viral barrier capabilities and minimizing the collapse of micropores that decreases breathability and moisture vapor transmission rate.

Figure 3A:
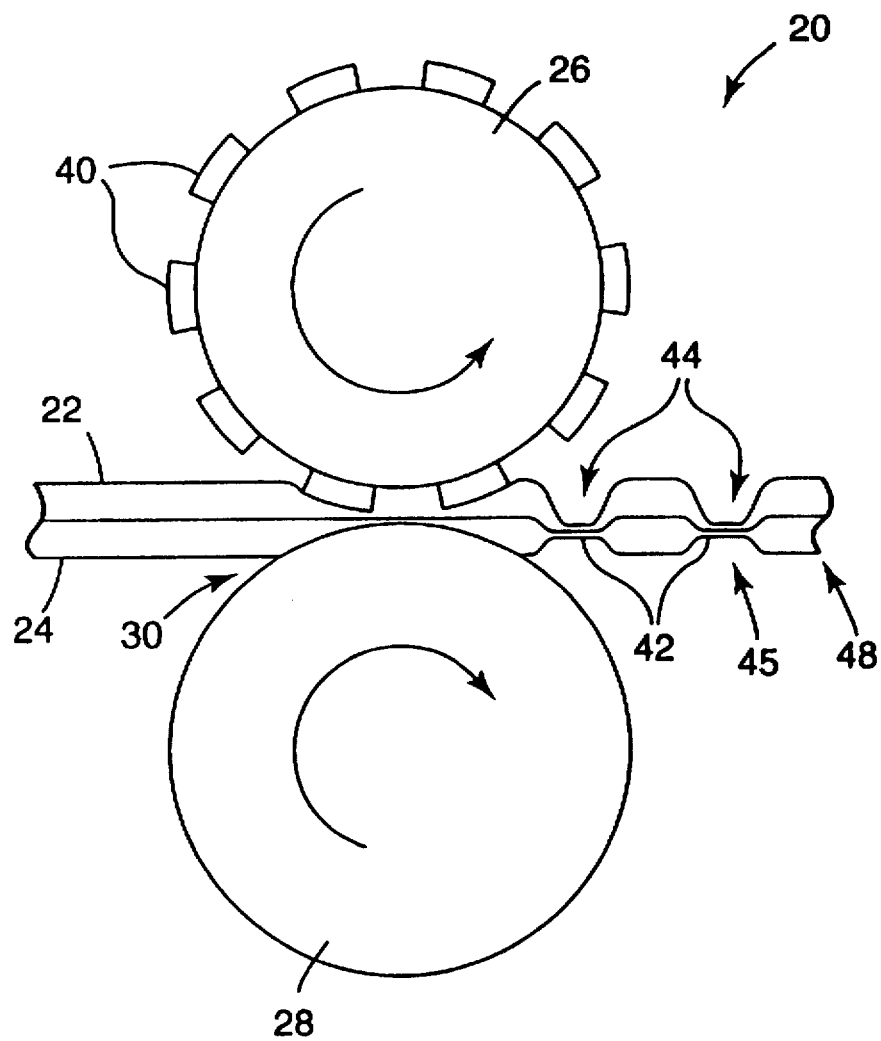
FIG. 3A illustrates a method for manufacturing a thermally bonded bilaminate viral barrier composite.

FIG. 3A is a schematic illustration of a calendering system 20 for laminating a web 22 to a microporous membrane 24 using heat, pressure and a pattern roll 26. The web 22 and microporous membrane 24 move between the heated metal pattern roll 26 and a heated metal smooth roll 28 in the direction of the arrows. Alternatively, the smooth roll may be rubber or some other resilient material heated by an external source. The surface speed of the rolls 26, 28 are approximately the same at the nip point 30. The spunbond web 22 is preferably interposed between the membrane 24 and the pattern roll 26, although it will be understood that the arrangement of the materials 22, 24 may be reversed.

Figure 5:
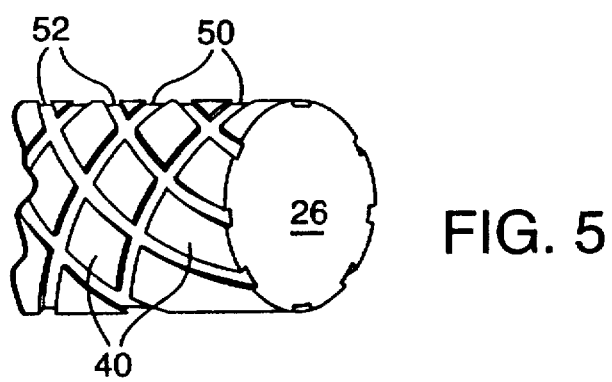
FIG. 5 is a sectional view of an exemplary pattern roll for use in manufacturing a thermally bonded viral barrier composite.

The resulting bilaminate viral barrier composite 48 has a matrix of point bonds 42 and indentations 44 corresponding to the pattern of point sources 40 on the pattern roll 26 (see exemplary point bonding roll of FIG. 5). In an embodiment where the web 22 is a spunbond nonwoven thermoplastic material, the fibers of the spunbond web are compressed and extruded under the point sources 40 and converted into a non-porous film. The micropores (not shown) in the microporous membrane 24 at the point bonds 42 are generally collapsed. The point sources 40 generally extend into the microporous membrane 24, compressing the microporous membrane and forming corresponding, although generally smaller, indentations 45 on the opposite side of the viral barrier composite 48.

Figure 3B:
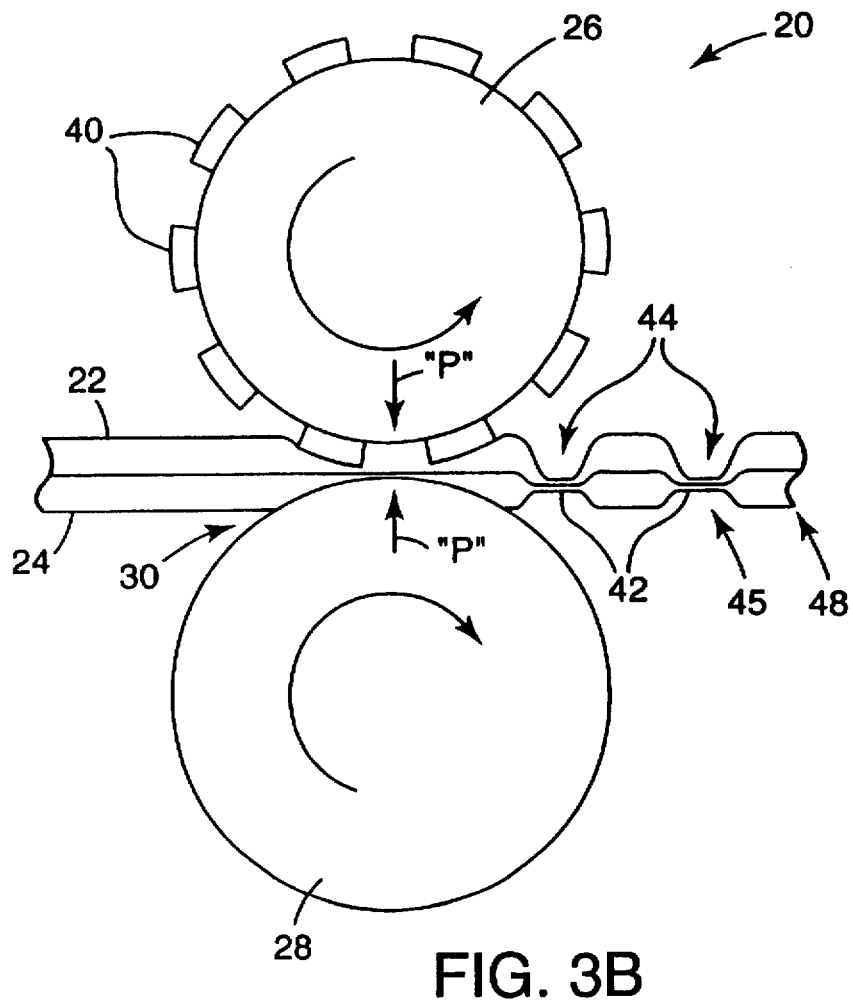
FIG. 3B illustrates an alternate method for manufacturing a thermally bonded bilaminate viral barrier composite.

The gap between the rolls 26, 28 may either be fixed or maintained as a function of the pressure "P" on the viral barrier composite 48. FIG. 3B illustrates the calendering system 20 configured so that the gap between the rolls 26, 28 is determined by the pressure "P" between the rolls 26, 28 and the resiliency of the viral barrier composite 48. It will be understood that the configuration of FIG. 3B may also be used to form a trilaminate viral barrier composite 49 or various multilayered composites.

Figure 3C:
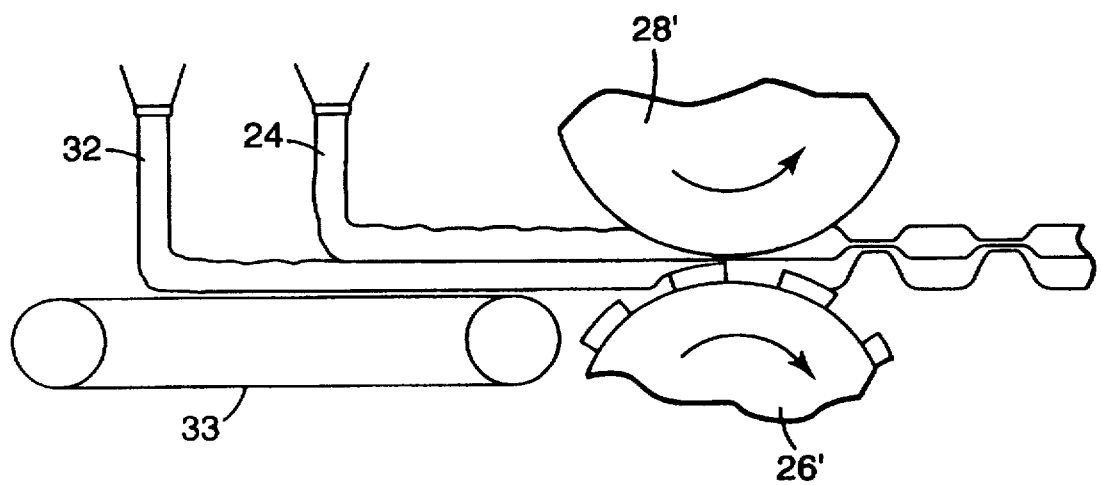
FIG. 3C illustrates a method for combining the step of bonding spunbond fiber with forming a thermally bonded bilaminate viral barrier composite.

FIG. 3C is an alternate embodiment in which unbonded spunbond fibers 32 extruded onto a moving support structure 33 are calendered to the viral barrier film 24 between a heated pattern roll 26' and a heated smooth roll 28'. It will be understood that this embodiment essentially simultaneously bonds and laminates the unbonded spunbond fibers 32 to the viral barrier film 24.

Figure 4:
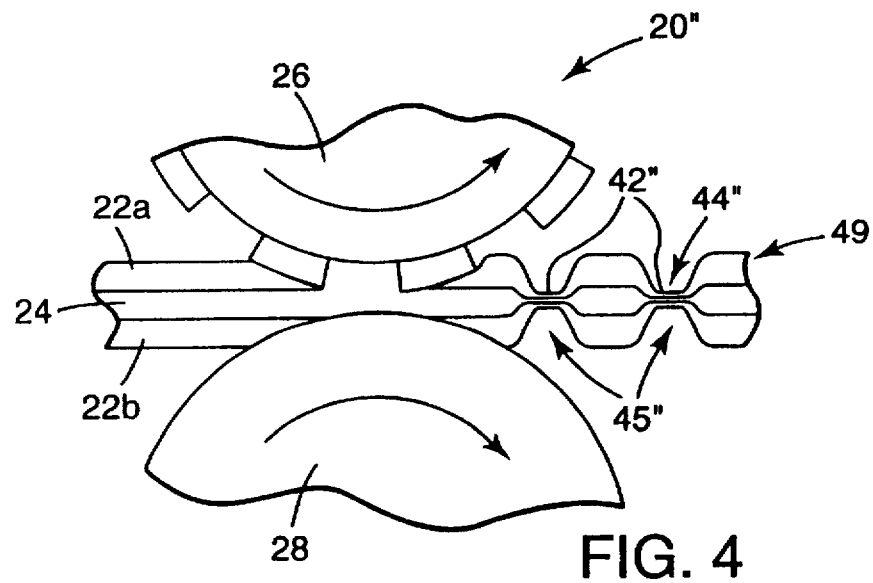
FIG. 4 illustrates a method for manufacturing a thermally bonded trilaminate viral barrier composite.

FIG. 4 is a schematic illustration of a thermal calendering system 20" for creating a trilaminate viral barrier composite 49. The system 20" simultaneously laminates webs 22a, 22b to opposite sides of the microporous membrane 24. As discussed in connection with FIGS. 3A and 3B, the pattern roll 26 compresses the webs 22a, 22b, and microporous membrane 24 at point bonds 42", creating a matrix of indentations 44", 45" in the viral barrier composite 49. It will be understood that the present method and apparatus for creating a viral barrier composite is not limited to composites of two or three layers. For example, a composite with four or more layers alternating between microporous membrane 24 and web 22a, 22b may be desirable for some applications.

FIG. 5 illustrates in the exemplary point bonding roll 26 having a pattern of grooves 50, 52 machined or etched into the outside surface of the roll 26. The grooves 50, 52 create a plurality of diamond shaped point sources 40 for use in the calendering systems 20, 20' discussed above. It will be understood that the present invention is not limited by the particular shape or arrangement of the point sources 40 and that a variety of continuous or intermittent relief patterns on the roll 26 are possible.

The micropores in the membrane 24 are generally collapsed by the point sources 40 at the bonding points 42, 42". Additionally, the viral barrier composite is stiffened at the bonding points. Therefore, the percent bond area on the point bonding roll 26 preferably is minimized, while maintaining adequate bond strength. The point sources 40 generally encompass between 7–30% of the total surface of the pattern roll 26. Additionally, in order to minimize point pressures which create pinholes in the microporous membrane 24, the density of point sources 40 is on the order of 1.75/cm$^2$ to 150 points/cm$^2$ with an average point size of approximately 4.0 to 0.20 mm$^2$, respectively.

The uniform nip pressure, line speed and roll temperatures are critical to maintaining the integrity of the viral barrier by minimizing pinholes, minimizing damage to the breathability of the microporous membrane, and creating a composite material with adequate bond strength. Although the interrelation of these parameters will be discussed in detail below, line speed may be in the range of 3–200 meters/minute and generally 20–100 meters/minute, with roll temperatures in the range of 100°–200° C.

Figure 6:
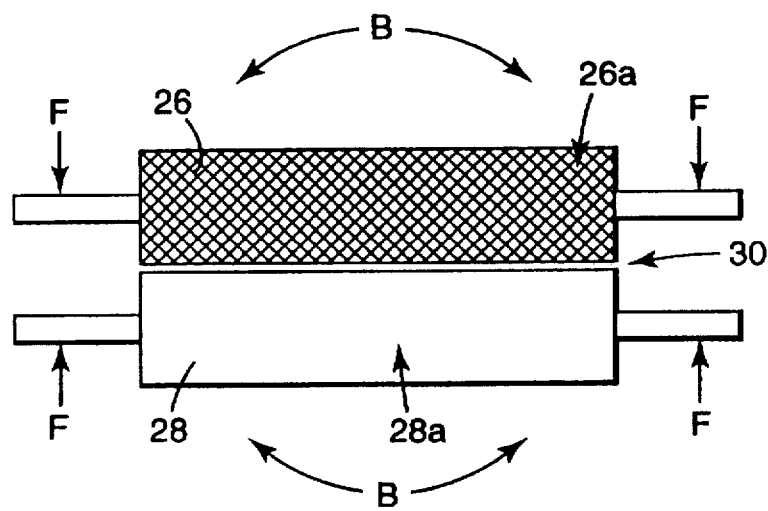
FIG. 6 is a front view of the calendering rolls of FIG. 3.

FIG. 6 illustrates the difficulty of maintaining uniform nip pressure across the complete width of the rolls 26, 28. In particular, when forces "F" are placed on opposite ends of the rolls 26, 28, a bending moment "B" is created such that the pressure along the nip point 30 may decrease in the center portions 26a, 28a of the rolls 26, 28. Rolls capable of creating a uniform pressure of 5–50N/mm across the nip point 30 are available from New Era Converting Machine, Inc. of Hawthorne, N.J.; Webex, Inc. of Neenah, Wis.; Kusters of Spartanburg, S.C.; B. F. Perkins of Chicopee, Mass.; and Ramisch (Greenville Machinery Corp.) of Greer, S.C.

In evaluating the materials of the present invention and the comparative materials, the following test methods were used.

Bond Strength

Bond Strength was measured using an "Instron Model 1122 Tensile Tester" for Examples 4–6 and Comparison Examples C, D, F or "Instron Model 4465 Table Mounted Universal Testing Instrument" for Examples 2, 3, 5, 7, and 8 from Instron Corporation, Canton, Mass. or "Hounsfield H10KM Universal Testing Machine" for Example 1 and Comparison Examples A-B from Hounsfield Test equipment, Croydon, England. The gage length was set at 25 mm and the crosshead speed was 304 mm/min. A sample was cut from the bilaminate or the trilaminate 25 mm wide and approximately 127 mm long, in the machine direction. The delamination of the sample was initiated by hand to insure that delamination would occur. The ends of the sample were clamped into the jaws of the instrument and mechanically separated at a 180° peel. The average separation value was recorded from the chart recorder for the distance of the bond. The mode of failure was recorded as peel, elongate, delaminate, or tear. For trilaminates, both bond sites were tested.

Porosity

Porosity was measured according to ASTM-D726-58 Method A and was reported in Gurley seconds required for 50 cc of air to permeate 6.5 cm$^2$ (one square inch) of fabric. Gurley is a coarse screening test used prior to the more expensive MVTR or Viral Penetration tests discussed below.

Pinhole Test

The number of pinholes were counted using a method generally corresponding to modified ASTM ES 21-1992. Modification includes using a larger test area, 50.8 cm$^2$. The presence of pinholes in fabric or plastic film for 50.8 cm$^2$ area was determined using a test fluid at 0.0138 MPa (2 psi) for 60 seconds.

Moisture Vapor Transmission Rate (MVTR)

Moisture vapor transmission rates (MVTR) were made using ASTM-E96-80 Upright Water Method, low humidity on one side and high humidity on the other. A 100 ml glass jar with a 3.81 cm diameter hole centered in a screw-on cap was filled with 50 ml of water. Three 38 mm diameter samples were die cut from the composite area. Each sample was centered over the adhesive side of a 5.07 cm$^2$ area hole of a foil adhesive ring. The sample and foil ring hole were lined up with a second foil ring with a 5.07 cm$^2$ area hole forming a foil/sample/foil assembly that was flat, wrinkle-free and that had no void areas in the sample area. A 4.445 cm diameter rubber washer was placed on the jar lid. The foil/sample/foil assembly was placed on the rubber washer with the film side of the sample up. The screw on cap was placed loosely on the jar. The jars complete with assemblies were placed in a constant temperature and relative humidity chamber for four hours at 40° C.±1° C. and 20±2 percent relative humidity. The screw on cap was tightened so that sample material was level with the cap and the rubber washer was seated. The jars were removed from the chamber after four hours and weighed to the nearest 0.01 gram ($W_1$=initial weight). The jars were returned to the chamber for at least 18 hours. After at least 18 hours the jars were removed from the chamber and weighed again ($W_2$=final weight). The moisture vapor transmission rate in grams/meter$^2$ in 24 hours was calculated for each sample using the following:

$$MVTR = \frac{(W_1 - W_2)4.74 \times 10^4}{T(hours)}$$

The three readings for each sample were averaged and reported to the nearest gram.

Resistance to Viral Penetration by a Blood-Borne Pathogen

The viral barrier properties of a composite was determined by ASTM Test Method ES 22-92. Basically, this test indicates whether a virus-containing liquid penetrates the test material. A test pressure of 13.8 kPa (2 psi) is applied throughout the liquid to the test material. The non-liquid-containing side of the test material is then swabbed and the swabbed exudate is cultured for 24 hours. The number of viruses is then counted. The test material has distinguishable viral barrier properties if the number of viruses is less than 100 for each sample tested. However, the number of viruses is preferably less than about 10, more preferably zero for each sample tested.

Viral Resistant Seam

The present invention is also directed to a low surface area reinforced viral resistant seam for protective apparel. The low surface area seam is designed to provide adequate tensile strength and enhanced comfort to the user. The method and apparatus for creating a comfortable reinforced viral resistant seam includes an ultrasonic welding wheel which permits much higher manufacturing speeds than other wheel designs.

Figure 7:
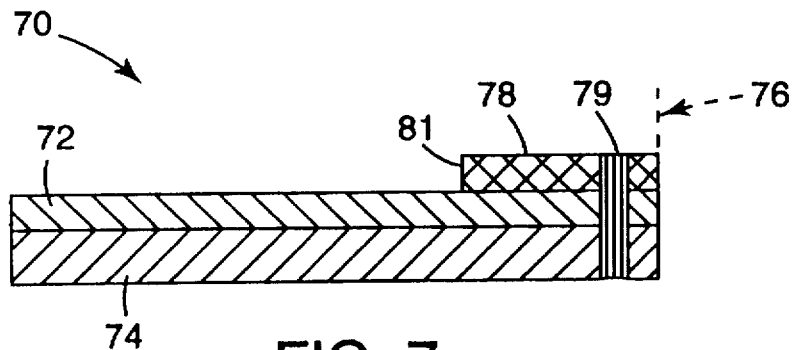
FIG. 7 is a schematic illustration of a low surface area reinforced viral resistant seam.
Figure 10:
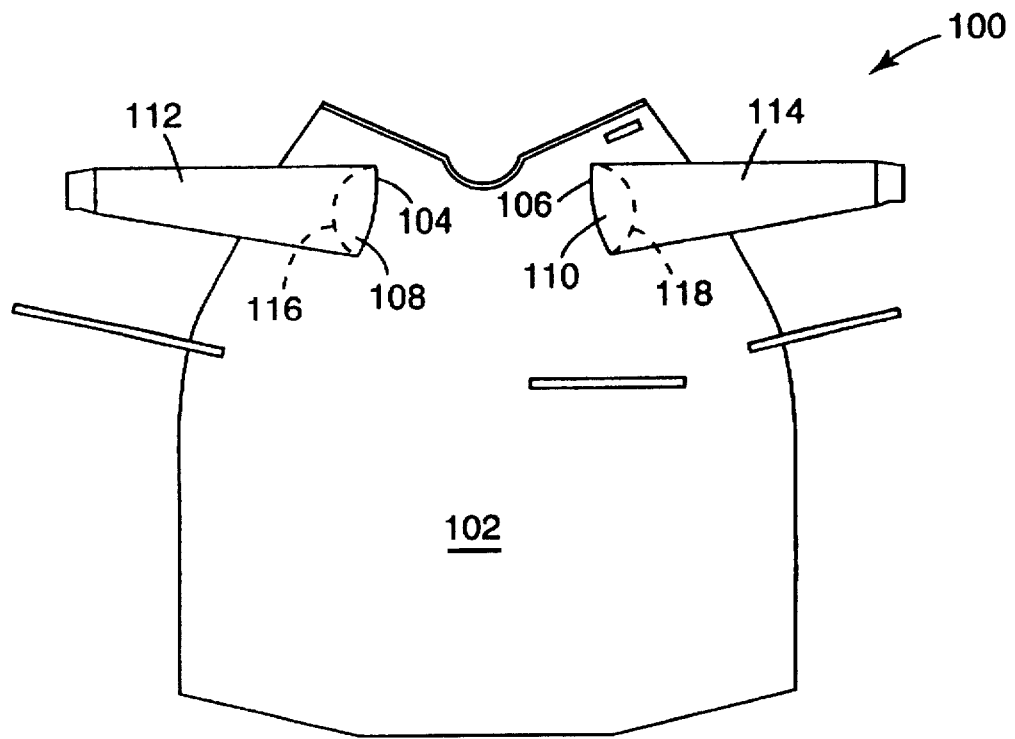
FIG. 10 is an illustration of an exemplary surgical gown with reinforced viral barrier seams.

FIG. 7 is a schematic illustration of an exemplary reinforced viral resistant seam 70 for an exemplary article of protective apparel (see e.g., FIG. 10). First and second webs 72, 74 are arranged to form a sealed edge 76. A reinforcing strip 78 is placed on one side of the sealed edge 76 during an ultrasonic welding process, which is discussed in detail below. It will be understood that more than one reinforcing strip 78 may be used for the seam 70 and that the location of the strip 78 may vary. For example, the reinforcing strip 78 may be located in-between or on either side of the webs 72, 74. The welding site 79 is immediately adjacent to the sealed edge 76 and preferably is within 0.794–6.35 mm (¹/₃₂" to ¼") of the sealed edge 76. Since the distal end 81 of the reinforcing strip 78 is not subject to the welding process, it remains soft, pliable and comfortable for the wearer.

The webs 72, 74 and reinforcing strip 78 may be constructed from a variety of woven or nonwoven materials having a thermoplastic component, as discussed above. Other microporous films with desirable breathability and moisture vapor transmission rates include: oriented particle films such as those described in U.S. Pat. No. 4,777,073, U.S. Pat. No. 4,347,844, U.S. Pat. No. 5,176,953, and U.S. Pat. No. 5,317,035; cold dense films made porous by hot and cold stretching such as those described in U.S. Pat. No. 5,013,439, U.S. Pat. No. 3,839,240, U.S. Pat. No. 3,426,754, U.S. Pat. No. 3,843,761, U.S. Pat. No. 3,801,404, and U.S. Pat. No. 3,801,692; and other thermally induced phase separated films such as described in U.S. Pat. No. 4,867,881, U.S. Pat. No. 4,539,256 and U.S. Pat. No. 4,519,909, all of which are hereby incorporated by reference.

Figure 8:
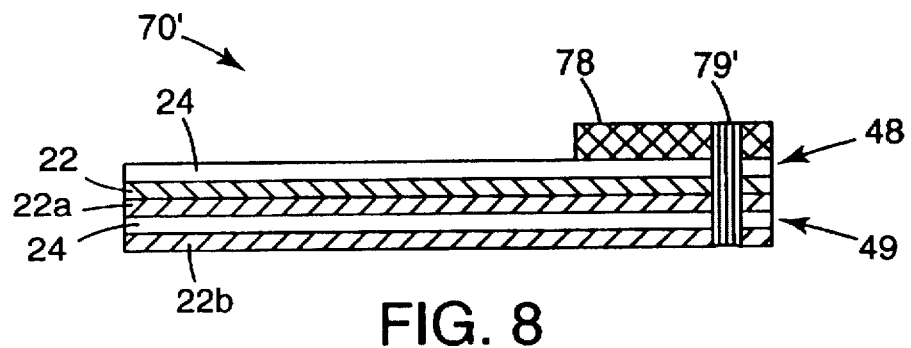
FIG. 8 is a schematic illustration of an alternate low surface area reinforced viral resistant seam.

FIG. 8 illustrates an alternate viral resistant seam 70' utilizing the viral barrier composites 48, 49. The spunbond web 22 of the viral barrier composite 48 is arranged to engage the spunbond webs 22a on the trilaminate composite viral barrier 49. The reinforcing strip 78 is arranged adjacent to the microporous membrane 24 on the bilaminate 48. The reinforcing strip may be a woven or non-woven web constructed predominately from polypropylene fibers or a film. A 136 gram/ m$^2$ (4 ounce/yard$^2$) non-woven polypropylene web suitable for use as the reinforcing strip is available from Poly-Bond, Inc. under part number 06525. It will be understood that a variety of other materials thermally bondable to the viral barrier composites 48, 49 may be suitable for the reinforcing strip 78.

In order to achieve a strong weld 79' along the seam 70', a portion of the bilaminate and trilaminate viral barrier composites 48, 49 and the reinforcing strip 78 are energized to a molten state by the ultrasonic welding process, which will be discussed below. The molten thermoplastic material flows around and adheres to the non-molten fibers of the spunbond nonwoven webs 22, 22a, 22b laminated to the microporous membrane 24.

The optimum quantity of energy transmitted by the ultrasonic generator is a function of dwell time under the ultrasonic welding wheel, the gap between the welding wheel and the ultrasonic generator, amplitude of the ultrasonic generator and the mass and composition of the material being welded. For a given viral barrier film or composite, excess ultrasonic energy at weld site may weaken the material. It is believed that a reinforcing strip 78 thermally bondable with the bilaminate 48 and trilaminate 49 provides additional material mass to the weld area that decreases the possibility that the microporous membrane 24, and its viral barrier capabilities, will be degraded by the welding process.

Figure 9A:
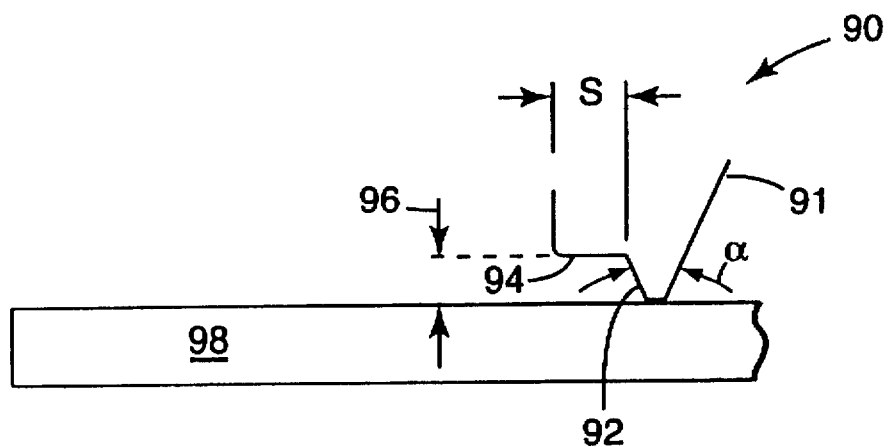
FIG. 9A is a schematic illustration of an apparatus for creating a reinforced viral resistant seam.

FIG. 9A is a schematic illustration of an ultrasonic welding system 90 suitable for forming viral resistant seam 70, 70'. Welding wheel 91 has a cutting edge 92 immediately adjacent to a solid seal area 94. The solid seal area 94 preferably has a width "s" of approximately 1.524 mm (0.060"). The cutting edge 92 has a V-shape having an angle α of approximately 60°. An ultrasonic welding unit capable of operating according to the present invention is available from Sonobond Corporation of Westchester, Pa., under model number LM-920. It will be understood that a variety of commercially available ultrasonic welding units may be suitable for this purpose.

The critical dimension or gap 96 between the solid seal area 92 and an ultrasonic generator 98 is a function of the thickness and composition of the webs 72, 74 and the reinforcing strip 78, the amplitude of oscillation and the rate at which the material passes under the welding wheel 91. Additionally, wheel pressure must be adequate to cut while welding or produce an easily removable trim. Finally, the peak to peak amplitude of oscillation is generally in the range of gap. Specific examples are set forth below.

It has been found that the welding speed also significantly impacts the sleeve seam tensile strength and the number of pinholes created. Slower speeds typically increase tensile strength and decrease pinholes. Slower welding speeds increase tensile strength and a higher amplitude also typically increases tensile strength. There appears to be an upper limit beyond which the output amplitude can be set without creating excessive pinholes. It is believed that the transition takes place at an amplitude range above 0.0762 mm (0.004 inches).

For the seam 70' of FIG. 8 constructed of the viral barrier composites 48, 49, the solid seal area 94 of the welding wheel 91 extrudes molten polypropylene into the spunbond fibers adjacent to the welding site 79'. The gap 96 between the solid seal area 94 on the welding wheel 91 and ultrasonic generator 98 affects the degree to which the spunbond fibers near the seam 70' are weakened, as well as how much molten thermoplastic material is produced by the welding process. If the gap 96 is too small, the fibers near the weld area will degrade, thereby weakening the viral barrier composites 48, 49 and the seam 70'. If the gap 96 is too large, not enough molten thermoplastic material will be produced and the resulting seam 70' will be weak.

FIG. 10 is an exemplary article of protective apparel 100 for which the present method and apparatus can be utilized. The protective apparel 100 has a body portion 102 with a pair of sleeve attachment edges 104, 106 to which an open end 108, 110 of first and second sleeve 112, 114 can be attached, respectively. It has been found that sleeve attachment seams 116, 118 preferably have a tensile strength in excess of five pounds per inch. In the present exemplary embodiment, the sleeves 112, 114 may be constructed of the trilaminate composite 49 to provide comfort and a greater base strength, while the body portion 102 may be constructed from a bilaminate composite 48 to minimize cost and weight. The average seam strength of the present reinforced viral resistant seams 70, 70' is typically 7.5 pounds per inch and is in a range generally between 5.7 to 9.3 pounds per inch, as will be discussed in the Examples detailed below. It will be understood that the present reinforced viral resistant seams 70, 70' may be used for any seams of the protective apparel 100.

Objects and advantages of this invention are further illustrated by the following examples, but the particular materials and amounts thereof recited in these examples as well as other conditions and details, should not be construed to unduly limit this invention. All materials are commercially available except where stated or otherwise made apparent.

EXAMPLES

Example 1

A bilaminate was prepared by thermally point bonding a 0.0305 mm microporous membrane prepared as described in Example 9 of U.S. Pat. No. 5,260,360 to Mrozinski et al. dated Nov. 9, 1993 except the blend ratio of materials was 62.5/1.5/2.5/33.5, PP/FCO/BLUE RED 8515 from Hoechst-Celanese, Charlotte, N.C./MO to a 33.9 g/m$^2$ polypropylene spunbond nonwoven web commercially available as Style No. 341, 33.9 g/m$^2$, sky blue color from Poly-Bond, Inc., Waynesboro, Va. The conditions for thermal point bonding the membrane are in Table 1. The membrane was in contact with the heated smooth roll and the nonwoven web in contact with the heated pattern roll. The web width was approximately 1.66 meters. The steel pattern roll had a diamond point bonding pattern. The point bonding represented approximately 20% bonding surface area, 21.7 points/cm$^2$, and individual bond point size of 0.8 mm$^2$. The bilaminates were tested for machine direction bond strength, porosity (Gurley), pinholes, viral barrier properties, and MVTR. The test methods are described above and the test results are in Table 2. At least three tests were performed for each test method.

Comparison Example A

The bilaminate was prepared and tested as described in Example 1 using the conditions in Table 1. The test results are in Table 2. This example represents the same conditions as Example 1 except an increase in the smooth roll temperature which caused the bilaminate to increase bond strength, lose porosity, and increase number of pinholes.

Example 2

The bilaminate was prepared and tested as described in Example 1 using the conditions in Table 1. The test results are in Table 2.

Comparison Example B

The bilaminate was prepared and tested as described in Example 1 using the conditions in Table 1. The test results are in Table 2. This example represents the same conditions as Example 2 except a decrease in the roll temperatures and the subsequent decrease in bond strength.

Example 3

The bilaminate was prepared and tested as described in Example 1 using the conditions in Table 1, except the diamond point bonding represented approximately a 21.6% bonding surface area, 51.0 points/cm$^2$, and individual bond point size of 0.42 mm$^2$. The test results are in Table 2.

Example 4

The bilaminate was prepared and tested as described in Example 1 using the conditions in Table 1, except the diamond point bonding represented approximately a 21.6% bonding surface, 51.0 points/cm², and individual bond point size of 0.42 mm². The test results are in Table 2.

Comparison Examples C and D

The bilaminate was prepared and tested as described in Example 1 using the conditions in Table 1, except the diamond point bonding represented approximately a 21.6% bonding surface, 51.0 points/cm², and individual bond point size of 0.42 mm². The test results are in Table 2. These examples represent the same roll temperatures and pressure as Example 4 with a decrease in the line speed and the subsequent increase in number of pinholes and increase in bond strength.

Example 5

Ten samples of the bilaminate was prepared and tested as described in Example 1 using the conditions in Table 1, except the diamond point bonding represented approximately a 17–20 percent bonding surface. A 2 meter wide calender that had a 1 mm crowned smooth roll was gapped by putting shimstock between the bearing housings of the rolls. This provided a gap of approximately 2 mils between the rolls on the outer 450–500 mm edges of the web. The outer 500 mm along one edge of the material that was tested and the test results are in Table 2.

Example 6

The bilaminate was prepared and tested as described in Example 1 using the conditions in Table 1, except the diamond point bonding represented approximately a 15% bonding surface. A gap was set between the two steel rolls. The web width was approximately 0.5 meters. The test results are in Table 2.

TABLE 1

| Examples | Pattern Roll Temperature (°C.) | Smooth Roll Temperature (°C.) | Pressure (N/mm) | Line Speed (m/min.) |
|---|---|---|---|---|
| 1 | 145 | 140 | 15 | 52 |
| A | 143 | 150 | 15 | 52 |
| 2 | 148 | 146 | 10 | 67 |
| B | 135 | 130 | 10 | 67 |
| 3 | 151 | 142 | 15 | 52 |
| 4 | 135 | 135 | 50 | 100 |
| C | 135 | 135 | 50 | 65 |
| D | 135 | 135 | 50 | 30 |
| 5 | 135 | 130 | 0.0254 mm gap¹ | 27 |
| 6 | 142 | 116 | 0.0254 mm gap¹ | 9 |

¹a gap was set between the rolls instead of using pressure to keep the rolls together.

TABLE 2

| Examples | Average Bond Strength (N/cm) | Porosity (Gurley) (sec/50 cc) | Pinholes per no. samples | Viral Barrier (failed samples per samples tested) | MVTR (g/m²/24 hrs) |
|---|---|---|---|---|---|
| 1 | 0.200 | 74.1¹ | 0/9 | 1/27 | 7340 |
| A | 1.4 | ∞ | 5/9 | Not tested | — |
| 2 | 0.159 | 140 | 0/9 | 0/33 | — |
| B | 0.025 | 134 | 0/9 | Not tested | — |
| 3 | 0.403 | 59 | 2/35 | 0/28 | 7674 |
| 4 | 0.123 | 116 | 1/3 | Not tested | — |
| C | 0.193 | 108 | 4/3 | Not tested | — |
| D | 0..298 | 120 | 8/3 | Not tested | — |
| 5 | 0.355 | 115 | 1/9 | 0/27 | — |
| 6 | 0.385 | 83 | 0/9 | Not tested | — |

¹Microporous membrane had Gurley of approximately 60 sec/50 cc prior to lamination.

Example 7

Trilaminates were prepared by thermally point bonding a 0.0305 mm microporous membrane prepared as described in Example 9 of U.S. Pat. No. 5,260,360 to Mrozinski et al. dated Nov. 9, 1993 except the blend ratio of materials was 62.5/1.5/2.5/33.5, PP/FCO/BLU; RED 8515 from Hoechst-Celanese, Charlotte, N.C./MO to a 33.9 g/m² polypropylene spunbond nonwoven web commercially available as Style No. 341, 33.9 g/m², sky blue color from Poly-Bond, Inc., Waynesboro, Va. The conditions for bonding the membrane to the web are in Table 3. One web was next to the heated smooth steel roll and the other web next to the heated pattern roll with the membrane between the two webs. The web widths were approximately 1.66 meters. The steel pattern roll had a diamond point bonding pattern which represented approximately 20% bonding surface area, 21.7 points/cm², and individual bond point size of 0.8 mm². The trilaminates were tested for machine direction bond strength, pinholes, viral barrier properties, and MVTR. The test methods are described above and the test results are in Table 4.

Example 8

The trilaminate was prepared and tested as described in Example 7 using the conditions in Table 3, except the diamond point bonding represented approximately a 21.6% bonding surface, 51.0 points/cm², and individual bond point size of 0.42 mm². The test results are in Table 4.

TABLE 3

| Examples | Pattern Roll Temperature (°C.) | Smooth Roll Temperature (°C.) | Pressure (N/mm) | Line Speed (m/min) |
|---|---|---|---|---|
| 7 | 150 | 150 | 10 | 37 |
| 8 | 142 | 155 | 20 | 52 |

TABLE 4

| Examples | Average Bond Strength Pattern Roll Side (N/cm) | Average Bond Strength Smooth Roll Side (N/cm) | Pinholes (number per number of samples) | Viral Barrier (number of failures per number of samples) | MVTR (g/m²/24 hrs) |
|---|---|---|---|---|---|
| 7 | 0.123 | 0.173 | 0/9 | 1/16 | — |
| 8 | 0.215 | 0.292 | 3/70 | 2/20 | 7330 |

Example 9

Seams were formed as illustrated in FIG. 8 using a trilaminate of a microporous membrane prepared as described in Example 9 of U.S. Pat. No. 5,260,360 to Mrozinski et al. dated Nov. 9, 1993, except the blend ratio of materials was 62.5/1.512.5/33.5, PP/FCO/BLUE RED 8515 ( available from Hoechst-Celanese, Charlotte, N.C.)/ MO, thermally point bonded between two layers of a spunbond nonwoven polypropylene web commercially available as Style No. 341, 33.9 g/m², sly blue color from Poly-Bond, Inc., Waynesboro, Va., a bilaminate of the microporous membrane material thermally point bonded to one layer of the spunbond nonwoven polypropylene web so that the nonwoven side was in contact with the nonwoven of the trilaminate, and a reinforcing strip of a 135.6 g/m² (4 oz./sq. yd.) spunbond nonwoven polypropylene web commercially available as "Style: 06525 Industrial Spunbonded Polypropylene" from Poly-Bond, Inc. The thermal point bond conditions for the bilaminate and the trilaminate are in Table 5. These laminates were combined by ultrasonic welding using an ultrasonic welding unit commercially available as Model Number LM-920 from Sonobond Corporation, Westchester, Pa. with a welding wheel as shown in FIG. 9A. The welding wheel speed dial setting was 5, the horn speed setting was 5, the output setting was 5 and the pressure setting was 0.414 MPa (60 psi). The gap between the solid seal area and an ultrasonic horn is in Table 6. These settings produces seams with adequate tensile strength at welding speeds of up to 12.31 meters/minute (40 feet/minute). The weld tensile strength was determined using a modification of ASTM Test Method D5035-90 using an "Instron Model 1122 Tensile Tester" from Instron Corporation, Canton, Mass. The gage length was set at 5.08 cm (2 inches) and the crosshead speed was 304 mm/min. The seams were prepared so that the seam was tested in the direction perpendicular to the machine direction (cross machine direction). The results of the weld tensile strength test are shown in Table 6.

TABLE 5

Thermal Point Bond Conditions for:

|  | Bilaminate | Trilaminate |
|---|---|---|
| Pattern Roll Temperature (°C.) | 148 | 150 |
| Smooth Roll Temperature (°C.) | 140 | 150 |
| Pressure (Newton/millimeter) | 10 | 20 |
| Line Speed (meters/minute) | 67 | 50 |

Comparison Example G

Figure 9B:
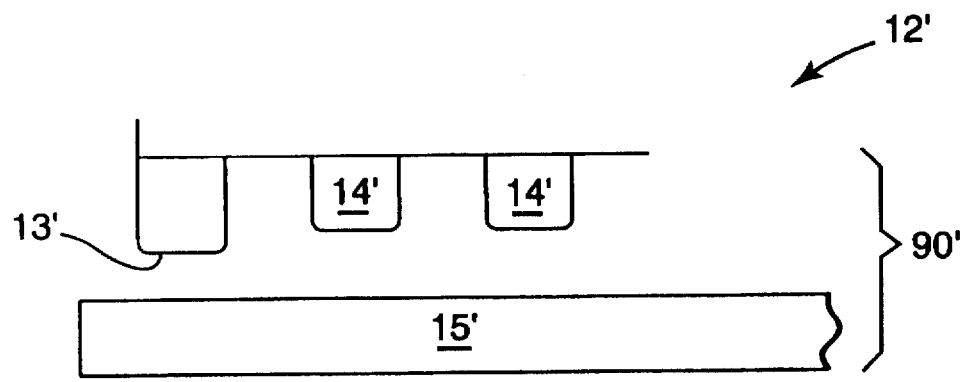
FIG. 9B is a schematic illustration of an alternate apparatus for creating a reinforced viral barrier seam used for testing the present welding concept on a variety of materials.

Seams were formed using the same bilaminate and trilaminate described for Example 9 without the reinforcing strip. The laminates were combined by ultrasonic welding as described in Example 9 except the welding wheel used is shown in FIG. 9B and the gap between the welding wheel and the horn was decreased to compensate for the different thickness without the reinforcing strip. The weld tensile strength was tested as in Example 9 and the results are shown in Table 6.

Example 10

Seams were formed using two bilaminates between two reinforcing strips described for Example 9. The laminate fabrics and strip were combined with the nonwoven sides of the laminate together by ultrasonic welding as described in Example 9 except the welding wheel used is shown in FIG. 9A and the gap between the welding wheel and the horn was increased to compensate for the different thickness of the laminates and the additional reinforcement strip. The weld tensile strength was tested as in Example 9 except the seams were prepared so that the seam was tested in the machine direction and results are shown in Table 6.

Comparison Example H

Seams were formed using two bilaminates without the reinforcing strip described for Example 9 using the welding wheel of FIG. 9B. The laminate fabrics were combined by ultrasonic welding as described in Example 9 except the gap between the welding wheel and the horn was decreased to compensate for the different thickness of the laminates without the reinforcing strip. The weld tensile strength was tested as in Example 9, except the seams were prepared so that the seam was tested in the machine direction. The results are shown in Table 6.

Example 11

Seams were formed using two polyethylene bilaminates commercially available as "Daltex CN4 Polyethylene Barrier Fabric" from Don and Low Nonwovens Ltd., Forfar, Scotland and a reinforcing strip made of 2 layers of clear, liner grade polyethylene bag material commercially available from Polar Plastics, Oakdale, Minn. The surface of the bag material was cleaned by wiping with a hexane soaked paper towel before welding. The laminate fabrics and reinforcing strip were combined by ultrasonic welding as described in Example 9 except the welding wheel used is shown in FIG. 9B and the gap between the welding wheel and the horn was adjusted to compensate for the different thickness of the laminates and the strip. The weld tensile strength was tested as in Example 9 and the results are shown in Table 6.

Comparison Example I

Seams were formed using two bilaminates without the reinforcing strip described for Example 11. The laminate fabrics were combined by ultrasonic welding as described in Example 9 except the welding wheel used is shown in FIG. 9B and the gap between the welding wheel and the horn was decreased to compensate for the different thickness of the laminates without the reinforcing strip. The weld tensile strength was tested as in Example 9 and the results are shown in Table 6.

Example 12

Seams were formed using two 30 grams per square yard nylon/rayon nonwoven diskette liners commercially available as "#9245" from Veratec, Walpole, Mass. and a reinforcing strip made from one layer of a polyester film commercially available as "PP2500 Transparency Film" from 3M, St. Paul, Minn. The nonwoven fabrics and strip were combined by ultrasonic welding as described in Example 9 except the welding wheel used is shown in FIG. 9B and the gap between the welding wheel and the horn was adjusted to compensate for the different thickness of the laminates and the strip. The weld tensile strength was tested as in Example 9 and the results are shown in Table 6.

Comparison Example J

Seams were formed using the two nonwoven fabrics without the reinforcing strip described for Example 12. The laminate fabrics were combined by ultrasonic welding as described in Example 9 except the welding wheel used is shown in FIG. 9B and the gap between the welding wheel and the horn was decreased to compensate for the different thickness of the laminates without the reinforcing strip. The weld tensile strength was tested as in Example 9 and the results are shown in Table 6.

TABLE 6

| Examples | Gap (mm) | Total Thickness (mm) | Weld Tensile Strength (N/cm) | Standard Deviation (N/cm) | Number of Samples Tested |
|---|---|---|---|---|---|
| 9 | 0.0635 | 0.889 | 17.14 | 4.15 | 20 |
| Comp. G | 0.0508 | 0.406 | 12.91 | 2.94 | 20 |
| 10 | 0.1461 | 1.270 | 20.31 | 1.75 | 25 |
| Comp. H | 0.0381 | 0.305 | 17.51 | 2.35 | 30 |
| 11 | 0.0762 | 0.508 | 4.71 | 0.84 | 22 |
| Comp. I | 0.0254 | 0.406 | 3.15 | 0.61 | 21 |
| 12 | 0.1016 | 0.483 | 1.10 | 0.35 | 24 |
| Comp. J | 0.0254 | 0.356 | 0.44 | 0.25 | 20 |

In general, reinforced seam welds are stronger than the same weld without reinforcing strips.

Although the invention has been described with respect to specific preferred embodiments, it should be appreciated that other embodiments utilizing the concept of the present invention are possible without departing from the scope of the invention. The invention, for example, is not intended to be limited to the specific webs disclosed in the preferred embodiments; rather the invention is defined by the claims and equivalents thereof.

What is claimed is:

1. A viral barrier composite comprising a breathable thermoplastic film thermally bonded on at least one side thereof to a breathable thermoplastic web, the viral barrier composite having viral barrier properties that permit less than 100 viruses to pass according to ASTM Method ES 22-1992, a moisture vapor transmission rate of at least 700 g/m$^2$/24 hours and a bond strength between the thermoplastic film and breathable thermoplastic web of at least 0.07 N/cm.

2. The viral barrier composite of claim 1 wherein the thermoplastic film comprises a thermoplastic polymer and a water- and oil-repellent fluorochemical compound that forms a microporous membrane with oleophobic and hydrophobic properties.

3. The viral barrier composite of claim 2 wherein the microporous membrane comprises polypropylene.

4. The viral barrier composite of claim 1 wherein air permeability expressed as Gurley porosity comprises less than 1000 seconds/50 cc.

5. The viral barrier composite of claim 1 wherein air permeability expressed as Gurley porosity comprises less than 500 seconds/50 cc.

6. The viral barrier composite of claim 1 wherein the thermoplastic web comprises a bonded spunbond nonwoven polypropylene web.

7. The viral barrier composite of claim 1 wherein less than 50 viruses are permitted to pass according to ASTM Test Method ES 22-1992.

8. The viral barrier composite of claim 1 wherein less than 10 virus are permitted to pass according to ASTM Test Method ES 22-1992.

9. The viral barrier composite of claim 1 wherein no virus are permitted to pass according to ASTM Test Method ES 22-1992.

10. An article of protective apparel constructed from the viral barrier composite of claim 1.

11. The article of protective apparel of claim 10 having at least one reinforced viral resistant seam, the viral resistant seam comprising:

a first viral barrier composite having a first attachment edge;

a second viral barrier composite having a second attachment edge arranged with the first composite viral barrier to form a common seam edge extending along the first and second attachment edges;

at least one reinforcing strip extending along the common seam edge constructed from a thermoplastic material thermally bondable with the first and second viral barrier composite; and an ultrasonic weld bonding the first and second attachment edges and the reinforcing strip generally extending along a sealed edge to form the reinforced viral resistant seam.

12. The viral resistant seam of claim 11 wherein the ultrasonic weld comprises a weld line offset less than 1.0 cm from the sealed edge.

13. A viral barrier composite comprising a breathable thermoplastic microporous membrane thermally bonded on at least one side thereof to a breathable thermoplastic nonwoven web, the viral barrier composite having viral barrier properties that permit less than 100 viruses to pass according to ASTM Method ES 22-1992 and a bond strength between the thermoplastic microporous membrane and the breathable thermoplastic nonwoven web of at least 0.07 N/cm.

14. The viral barrier composite of claim 13 wherein less than 50 viruses are permitted to pass according to ASTM Test Method ES 22-1992.

15. The viral barrier composite of claim 13 wherein the microporous membrane comprises a thermoplastic polymer and a water- and oil-repellent fluorochemical compound that forms a microporous membrane with oleophobic and hydrophobic properties.

16. The viral barrier composite of claim 13 wherein the thermoplastic microporous membrane and the breathable thermoplastic nonwoven web comprise polypropylene.

* * * * *

UNITED STATES PATENT AND TRADEMARK OFFICE
CERTIFICATE OF CORRECTION

PATENT NO. : 5,786,058
DATED : July 28, 1998
INVENTOR(S) : Sara L. Megchelsen, et. al.

It is certified that error appears in the above-identified patent and that said Letters Patent is hereby corrected as shown below:

Insert on
Title page, item [73], Assignee: should read -- Minnesota Mining and Manufacturing Company, St. Paul, Minnesota, U.S.A.--

Signed and Sealed this

Twenty-first Day of March, 2000

Attest:

Attesting Officer

Q. TODD DICKINSON

Commissioner of Patents and Trademarks